US009724313B2

(12) United States Patent
Skulachev

(10) Patent No.: US 9,724,313 B2
(45) Date of Patent: Aug. 8, 2017

(54) PHARMACEUTICAL COMPOSITION FOR USE IN MEDICAL AND VETERINARY OPHTHALMOLOGY

(75) Inventor: Maxim V. Skulachev, Moscow (RU)

(73) Assignee: MITOTECH SA, Luxembourg (LU)

( * ) Notice: Subject to any disclaimer, the term of this patent is extended or adjusted under 35 U.S.C. 154(b) by 160 days.

(21) Appl. No.: 13/315,397

(22) Filed: Dec. 9, 2011

(65) Prior Publication Data
US 2012/0094962 A1 Apr. 19, 2012

Related U.S. Application Data

(63) Continuation-in-part of application No. PCT/RU2009/000295, filed on Jun. 10, 2009.

(51) Int. Cl.
*A61K 31/201* (2006.01)
*A61K 31/122* (2006.01)
*A61K 9/00* (2006.01)

(52) U.S. Cl.
CPC .......... *A61K 31/122* (2013.01); *A61K 9/0048* (2013.01)

(58) Field of Classification Search
CPC ..... A61K 31/23; A61K 31/201; A61K 31/231
See application file for complete search history.

(56) References Cited

U.S. PATENT DOCUMENTS

| | | | |
|---|---|---|---|
| 5,538,974 | A | 7/1996 | Ogawa et al. |
| 6,331,532 | B1 | 12/2001 | Murphy et al. |
| 7,109,189 | B2 | 9/2006 | Murphy et al. |
| 2002/0044913 | A1 | 4/2002 | Hamilton |
| 2005/0065099 | A1 | 3/2005 | Walkinshaw et al. |
| 2007/0259908 | A1 | 11/2007 | Fujii et al. |
| 2007/0270381 | A1 | 11/2007 | Murphy et al. |
| 2008/0176929 | A1 | 7/2008 | Skulachev et al. |
| 2008/0275005 | A1 | 11/2008 | Murphy et al. |
| 2010/0273892 | A1* | 10/2010 | Miller et al. ................... 514/688 |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| RU | 2318500 C2 | 3/2008 |
| WO | 99/26582 A2 | 6/1999 |
| WO | 2004/014927 A1 | 2/2004 |
| WO | 2006/005759 A2 | 1/2006 |
| WO | 2007/046729 A1 | 4/2007 |
| WO | 2008048134 A1 | 4/2008 |
| WO | 2009/005386 A1 | 1/2009 |
| WO | 2009/158348 A1 | 12/2009 |

OTHER PUBLICATIONS

Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.
Clem et al. (2008) "Small-molecule inhibition of 6-phosphofructo-2-kinase activity suppresses glycolytic flux and tumor growth," Mol. Canc. Ther. 7(1):110-120.
Green (1974) "The electromechanochemical model for energy coupling in mitochondria," Biochimica et Biophysica Acta, 346:27-78.
Kirste et al. (1995) "Continuous-wave electron spin resonance studies of porphyrin and porphyrin-quinone triplet states," J. Chem. Soc. Perkin Trans. 2:2147-2152.
Murphy et al. (2007) Targeting antioxidants to mitochondria by conjugation to lipophilic cations. Annu. Rev. Pharmacol. Toxicol., 47:629-656.
Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.
Plotnikov et al. (2010) "New-generation Skulachev ions exhibiting nephroprotective and neuroprotective properties." Biochemistry (Mosc.), 75(2):145-150.
Skulachev et al. (2005) "Aging as mitochondria-mediated atavistic program. Can aging be switched off?" Ann. N.Y. Acad. Sci., 1057:145-164.
Skulachev et al. (2009) "An attempt to prevent senescence: a mitochondrial approach," Biochimica et Biophysica Acta., 1787:437-461.
Smith et al. (2008) "Mitochondria-targeted antioxidants in the treatment of disease,"Ann. N.Y. Acad. Sci., 1147:105-111.
Snow et al. (2010) "A double-blind, placebo-controlled study to assess the mitochondria-targeted antioxidant MitoQ as a disease-modifying therapy in Parkinson's disease," Mov. Disord. 25(11):1670-1674.
Stefanova et al. (2010) "Behavioral effects induced by mitochondria-targeted antioxidant SkQ1 in Wistar and senescence-accelerated OXYS rats," J. Alzheimer's Dis. 21:479-491.
Tauskela (2007) "MitoQ—a mitochondria-targeted antioxidant," I Drugs, 10:399-412.
Triet et al. (1993) "Anxiogenic stimuli in the elevated plus-maze," Pharmacol. Biochem. & Behay. 44:463-469.
Antonenko, Yu, et al., Mitochondria-Targeted Plastoquinone Derivatives as Tools to Interrupt Execution of the Aging Program. 1. Cationic Plastoquinone Derivatives: Synthesis and in vitro Studies (2008), Biochemistry (Mosc.), 73 (12):1273-1287.
Doughan, et al., Original Research Communication: Mitochondrial Redox Cycling of Mitoquinone Leads to superoxide Production and Cellular Apoptosis (2007), Antioxid. Redox Signal., 9(11):1825-1836.
Neroev, et al., Mitochondria-Targeted Plastoquinone Derivatives as Tools to Interrupt Execution of the Aging Program. 4. Age-Related Eye Disease. SkQ1 Returns Vision to Blind Animals (2008), Biochemistry (Mosc.), 73 (12):1317-1328.

(Continued)

*Primary Examiner* — Zohreh Fay
(74) *Attorney, Agent, or Firm* — Anne-Louise Kerner; Morse, Barnes-Brown & Pendleton, P.C.

(57) ABSTRACT

The invention relates to the manufacturing and use of pharmaceutical compositions of medicines (ophthalmic preparations) comprising a mitochondria-addressed antioxidant and a set of auxiliary substances providing effective treatment for ophtalmological diseases in humans and animals.

8 Claims, No Drawings

(56) References Cited

OTHER PUBLICATIONS

Skulachev, Clinical Review: How to Clean the Dirtiest Place in the Cell: Cationic Antioxidants as Intramitochondrial ROS Scavengers (2005), IUBMB Life, 57(4/5):305-310.

Skulachev, A Biochemical Approach to the Problem of Aging: "Megaproject" on Membrane-Penetrating Ions. The First Results and Prospects (2007), Biochemistry (Mosc.), 72(2):1385-1396.

International Search Report and Written Opinion of the International Searching Authority, PCT/RU2009/000295, 2/2512010, 7 pages.

PubChem compound CID 388445; Mar. 26, 2005 (Mar. 26, 2005) [retrieved from http://pubchem.ncbi.nlm.nih.gov/summary/summary.cgi?cid=38845&loc=ec_rcs on Jul. 31, 2012] whole doc (4 pages).

International Search Report and Written Opinion of the International Searching Authority, PCT/US12/40711, Aug. 20, 2012 (9 pages).

Adlam et al. (2005) "Targeting an antioxidant to mitochondria decreases cardiac ischemia-reperfusion injury," FASEB J., 19:1088-1095.

Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).

Anisimov (2007) "Molecular and Physiological Mechanisms of Aging," Antioksidanty, Nov. 27, 2007, [on line] http://imquest.alfaspace.net/BOOK/MFMA/mfma_39_2.htm?embedded=yes translated from Russian to English.

Antonenko et al. (2008) "Protective effects of mitochondria-targeted antioxidant SkQ in aqueous and lipid membrane environments," J. Membr. Biol., 222:141-149.

Becker (2004) "New concepts in reactive oxygen species and cardiovascular reperfusion physiology" Cardiovascular Research, 61:461-470.

Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.

Havens et al. (2006) "Regulation of Late G1/S Phase Transition and APCCdh1 by Reactive Oxygen Species," Mol. Cell. Biol., 26(12):4701-4711.

Holloszy (1998) "Longevity of exercising male rats: effect of an antioxidant supplemented diet," Mechanisms of Ageing and Development, 100:211-219.

King et al. (2004) "Mitochondria-derived reactive oxygen species mediate blue light-induced death of retinal pigment epithelial cells," Photochem. And Photobiol., 79(5):470-475.

Li et al. (2000) "Skeletal muscle respiratory uncoupling prevents diet-induced obesity and insulin resistance in mice," Nat. Med. 6(10):1115-1120.

Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.

Longo et al. (2005) "Programmed and altruistic ageing," Nature Reviews Genetics 6:866-872.

Kirschner et al. (1994) "Role of iron and oxygen-derived free radicals in ischemia-reperfusion injury" J. Am. Coll. Surg., 179:103-117.

Popova et al. (2010) "Scavenging of Reactive Oxygen Species in Mitochondria Induces Myofibroblast Differentiation," Antiox. & Redox. Signal., 13(9):1297-1307.

Popova et al. (2006) "MitoQ induced miofibroblast differentiation of human fibroblasts," Biochimica et Biophysica Acta, S:433-434.

Reliene et al. (2007) "Antioxidants suppress lymphoma and increase longevity in atm-deficient mice," J. Nutrition, 137:229S-232S.

Reddy (2006) "Mitochondrial oxidative damage in aging and Alzheimer's disease: implications for mitochondrially targeted antioxidant therapeutics," J. Biomedicine and Biotech., Art.ID 31372:1-13.

Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.

Starkov et al. (1997) "6-ketocholestanol is a recoupler for mitochondria, chromatophores and cytochrome oxidase proteoliposomes," Biochim. Biophys. Acta. 1318:159-172.

Tompkins et al. (2006) "Mitochondrial dysfunction in cardiac ischemia-reperfusion injury: ROS from complex I, without inhibition," Dothan Biophys. Acta. 1762:223-231.

Sidorova et al. (2004) "Transcriptional activation of cytochrome P450 1A1 with alpha-tocopherol," Bull Exp. Bio. Med., 138(3):233-236.

Mecocci et al. (2000) "Plasma antioxidants and longevity: a study on healthy centenarians," Free Radical Biology and Medicine, 28(8):1243-1248.

Pozniakovsky et al. (2005) "Role of mitochondria in the pheromone- and amiodarone-induced programmed death of yeast,"J. Cell Biol., 168(2):257-69.

Orr et al. (2003) "Effects of overexpression of copper-zinc and manganese superoxide dismutases, catalase, and thioredoxin reductase genes on longevity in *Drosophila melanogaster*," J. Biol. Chem., 278(29):26418-26422.

Papp et al. (1999) "Glutathione status in retinopathy of prematurity," Free Radic. Biol. & Med., 27(7-8):738-743.

Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.

Petrosillo et al. (2006) "Protective effect of melatonin against mitochondrial dysfunction associated with cardiac ischemia-reperfusion: role of cardiolipin," FASEB J., 20:269-276.

Sheu et al. (2006) "Targeting antioxidants to mitochondria: a new therapeutic direction," Biochimica et Biophysica Acta, 1762:256-265.

Yildirim et al. (2005) "Role of oxidative stress enzymes in open-angle glaucoma," Eye, 19:580-583.

Zweier et al. (1987) "Direct measurement of free radical generation following reperfusion of ischemic myocardium," PNAS USA, 84:1404-1407.

Riess et al. (2004) "Reduced reactive O2 species formation and preserved mitochondrial NADH and [Ca2+] levels during short-term 17° C ischemia in intact hearts," Cardiovascular Research, 61:580-590.

Sundaresan et al. (1995) "Requirement for Generation of H2O2 for Platelet-Derived Growth Factor Signal Transduction," Science, 270:296-299.

International Search Report and Written Opinion of the International Searching Authority, PCT/RU2007/000044, Nov. 1, 2007 (9 Pages).

International Search Report dated Dec. 20, 2007 and International Preliminary Report on Patentability dated Nov. 10, 2009, PCT/RU2007/000171 (16 pages).

International Search Report and Written Opinion of the International Searching Authority, PCT/RU2007/000355, Mar. 27, 2008 (10 pages).

PCT International Search Report mailed Nov. 1, 2007 and International Preliminary Report on Patentability issued Aug. 4, 2009 for PCT Application No. PCT/RU2007/000043, 9 pages.

International Search Report and Written Opinion, PCT/RU2006/000547, dated Jul. 5, 2007 (7 pages).

PCT International Search Report and Written Opinion of the International Searching Authority for PCT Application No. PCT/RU2006/000546, mailed Jul. 5, 2007, 14 pages.

Lou et al. (2007) "Mitochondrial Uncouplers With an Extraordinary Dynamic Range," Biochem. J., 407:129-140.

International Search Report and Written Opinion, PCT/RU2009/000621, dated Aug. 12, 2010 (12 pages).

(56) References Cited

OTHER PUBLICATIONS

International Search Report and Written Opinion, PCT/RU2006/000394, dated Nov. 2, 2006 (6 pages).
Hansford et al. (1997) "Dependence of H2O2 formation by rat heart mitochondria on substrate availability and donor age," J. Bioenerg. Biomem. 29(1):89-95.
Brand et al. (1992) "The mechanism of the increase in mitochondrial proton permeability induced by thyroid hormones," Eur. J. Biochem. 206:775-781.
Blaikie et al. (2006) "Targeting Dinitrophenol to Mitochondria: Limitations to the Development of a Self-limiting Mitochondrial Protonophore," Biosci. Rep., 26:231-243.
Vlachantoni et al. (2011) "Evidence of severe mitochondrial oxidative stress and a protective effect of low oxygen in mouse models of inherited photoreceptor degeneration," Human Mol. Gen. 20(2):322-335.
13-Methoxydihydronitidine—Compound Summary PubChem compound CID 38845; Mar. 26, 2005 (Mar. 26, 2005) [retrieved_ from http://pubchem.ncbi.nlm.nih.gov/summary/summary.cgi?cid=38845&loc=ec_rcs on Jul. 31, 2012] whole doc (4 pages).
Bacsi et al. (2005) "Effect of pollen-mediated oxidative stress on immediate hypersensitivity reactions and late-phase inflammation in allergic conjunctivitis," J. Allergy Clin. Immunol., 116(4): 836-843.
Barclay et al. (2003) Phenols as antioxidants. In the Chemistry of Phenols, Part 2, Rappoport, Z Ed., Wiley, pp. 875 (3 pages).
Cherubini et al. (2005). Potential markers of oxidative stress in stroke. Free Radic Biol Med 39, 841-852.
Coulter et al. (2000) "Mitochondrially targeted antioxidants and thiol reagents," Free Rad. Biol. Med. 28 (10):1547-1554.
Denisov (2006) "Reactivity of quinones as alkyl radical acceptors," Kinetics and Catalysis, 45(5):662-671.
Dominguez (2006), "Ageing, lifestyle modifications, and cardiovascular disease in developing countries," J. Nutr. Health Aging, 10(2):143-149.
Galkina et al. (2004). "Endothelium-leukocyte interactions under the influence of the superoxide-nitrogen monoxide system." Med. Sci. Monit. 10:BR307-316.
Gear (1974) "Rhodamine 6G: A potent inhibitor of mitochondrial oxidative phosphorylation," J. Biol. Chem., 249 (11):3628-3637.
Giamarellos-Bourboulis et al. (2006). "Oleuropein: a novel immunomodulator conferring prolonged survival in experimental sepsis by Pseudomonas aeruginosa." Shock 26(14):410-416.
Giorgini et al. (2001) "Reactivity of ubiquinones and ubiquinols with free radicals." Free Rad. Res. 35:63-72.
Goldstein (2002) "Reactive oxygen species as essential components of ambient air," Biochemistry (Mosc.) 67:161-170.
Griffiths et al. (2001) "Genetic analysis of collagen-induced arthritis in rats: a polygenic model for rheumatoid arthritis predicts a common framework of cross-species inflammatory/autoimmune disease loci." Immunol. Rev. 184:172-83.
Haass et al. (2007) "Soluble protein oligomers in neurodegeneration: lessons from the Alzheimer's amyloid beta-peptide." Nat. Rev. Mol. Cell. Biol. 8:101-112.
Hummel et al. (1966) "Diabetes, new mutation in the mouse." Science, 153:1127-1128.
Hunter et al. (1979). "The Ca2+-induced membrane transition in mitochondria. I. The protective mechanisms." Arch. Biochem. Biophys. 195:453-459.
Johnson et al. (1980) "Localization of Mitochondria in Living Cells with Rhodamine 123," Proc. Natl. Acad. Sci. USA, 77(2):990-994.
Jolkkonen (2000) "Behavioral effects of the alpha(2)-adrenoceptor antagonist, atipamezole, after focal cerebral ischemia in rats," Eur. J. Pharmacol., 400, 211-219.
Juhaszova et al. (2004). "Glycogen synthase kinase-3beta mediates convergence of protection signaling to inhibit the mitochondrial permeability transition pore." J. Clin. Invest. 113:1535-1549.
Karl et al. (2003) "Behavioral phenotyping of mice in pharmacological and toxicological research," Exp. Toxicol. Pathol., 55(1):69-83.

Kirkinezos et al (2001) "Reactive Oxygen species and Mitochondrial Diseases," Seminars in Cell & Developmental Biology, 12:449-457.
Kroemer et al. (1995). "The biochemistry of programmed cell death" FASEB J. 9:1277-1287.
Li et al. (2002). "Activation of macrophage nuclear factor-kappa B and induction of inducible nitric oxide synthase by LPS." Respir. Res. 3:23 (6 pages).
Liu et al. (1996). "Induction of apoptotic program in cell-free extracts: requirement for dATP and cytochrome c." Cell 86:147-157.
Lysenko et al. (2001) "Thrombocytopathies and their role in the development of hemorrhagic syndrome in vascular diseases of the fundus oculi," Vestn. Oftalmol., 117(1):24-26 (English Translation of Russian article abstract—1 pages).
Maire et al. (2001) "Factors associated with hyperhomocysteinemia in Crohn's disease," Gastroenterol. Clin. Biol., 25 (8-9):745-748 (French-abstract only, 1 page).
Malenka et al. (1999) "Long-term potentiation: a decade of progress?" Science, 285(5435):1870-1874.
Matsumoto et al. (1992). "Antioxidant effect on renal scarring following infection of mannose-sensitive-piliated bacteria." Nephron. 60:210-215.
Monaco et al. (2004) "Canonical pathway of nuclear factor kB activation selectively regulates proinflammatory and prothrombotic responses in human atherosclerosis," PNAS, 101(15):5634-5639.
Mundi et al. (1991). "Extracellular release of reactive oxygen species from human neutrophils upon interaction with *Escherichia coli* strains causing renal scarring." Infect. Immun. 59(11):4168-4172.
Murphy et al. (2011) "Homocysteine in pregnancy," Adv. Clin. Chem., 53:105-37.
O'Hanley et al. (1996). "Prospects for urinary tract infection vaccines. In: Urinary Tract Infections: Molecular Pathogenesis and Clinical Management" (Mobley, H. L. T. & Warren, J.W., eds), (Washington, DC: ASM Press), pp. 405-425 (23 pages).
O'Hanley et al. (1991). "Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis." Infect. Immun. 59(3):1153-1161.
Okada et al. (2005) "The implications of the upregulation of ICAM-1/VCAM-1 expression of corneal fibroblasts on the pathogenesis of allergic keratopathy," Invest. Ophthalmol. Vis. Sci., 46(12):4512-4518.
Petit-Demouliere et al. (2005) "Forced swimming test in mice: a review of antidepressant activity," Psychopharmacol., 177:245-255.
Rodriguez-Spong et al. (2004) "General Principles of Pharmaceutical Solid Polymorphism: A Supramolecular Perspective," Advanced Drug Delivery Reviews, 56:241-274.
Saifer et al. (1957) "Laboratory Methods: The photometric microdetermination of blood glucose with glucose oxidase," J. Lab. Clin. Med., 51(3):448-460.
Sanmun et al. (2009) "Involvement of a functional NADPH oxidase in neutrophils and macrophages during programmed cell clearance: implications for chronic granulomatous disease," Am. J. Physiol. Cell Physiol. 297: C621-631.
Sarter (2002) Coenzyme Q10 and Cardiovascular Disease: A Review, J. Cardiovasc. Nurs. 16(4):9-20.
Selkoe (2002) "Alzheimer's disease is a synaptic failure," Science 298:789-791.
Smith, et al. (2003) "Delivery of bioactive molecules to mitochondria in vivo," PNAS, 100(9):5407-5412.
Spector (1995) "Oxidative stress-induced cataract: mechanism of action," FASEB J., 9:1173-1182.
Stella et al. (2007) Prodrugs: Challenges and Rewards, Springer, New York Part 1 and 2 (17 pages).
USDH (2005) "Guidance for Industry: Estimating the Maximum Safe Starting Dose in Initial Clinical Trials for Therapeutics in Adult Healthy Volunteers," U.S. Dept. of Health and Human Services, FDA, CDER (30 pages).

(56) References Cited

OTHER PUBLICATIONS

Viana et al. (2004) "Hypoglycemic and anti-lipemic effects of the aqueous extract from Cissus sicyoides," BMC Pharmacol. 4:9 (7 pages).

Villa et al. (2004) "Animal models of endotoxic shock" Meth. Mol. Med., 98:199-206.

Vollset et al. (2000) "Plasma total homocysteine, pregnancy complications, and adverse pregnancy outcomes: the Hordaland Homocysteine study," Am. J. Clin. Nutr., 71:962-968.

Zamzami et al. (1996), "Mitochondrial control of nuclear apoptosis," J. Exp. Med. 183:1533-1544.

Zoratti et al. (1995), "The mitochondrial permeability transition," Biochim. Biophys. Acta. 1241:139-176.

Zorov et al. (2000), "Reactive oxygen species (ROS)-induced ROS release: a new phenomenon accompanying induction of the mitochondrial permeability transition in cardiac myocytes," J. Exp. Med. 192(7):1001-1014.

Zorov et al. (2006), Mitochondrial ROS-induced ROS release: an update and review, Biochim. Biophys. Acta. 1757:509-517.

Bhate et al. (2008) "Vitamin B12 status of pregnant Indian women and cognitive function in their 9-year-old children," Food Nutr. Bull., 29:249-54.

Gorgone et al (2009) "Hyperhomocysteinemia in patients with epilepsy: does it play a role in the pathogenesis of brain atrophy? A preliminary report," Epilepsia, 50(1):33-36.

Molloy et al. (2009) "Maternal vitamin B12 status and risk of neural tube defects in a population with high neural tube defect prevalence and no folic Acid fortification," Pediatrics, 123:917-923.

Rogers (2008) "Has enhanced folate status during pregnancy altered natural selection and possibly Autism prevalence? A closer look at a possible link," Med. Hypoth., 71:406-410.

Ragnarsdottir et al. (2008). "TLR- and CXCR1-dependent innate immunity: insights into the genetics of urinary tract infections." Eur. J. Clin. Invest. 38(2):12-20.

\* cited by examiner

PHARMACEUTICAL COMPOSITION FOR USE IN MEDICAL AND VETERINARY OPHTHALMOLOGY

REFERENCE TO RELATED APPLICATIONS

This application is a continuation-in-part of International Application No. PCT/RU2009/000295, filed on Jun. 10, 2009, the entire disclosure of which is hereby incorporated by reference herein.

FIELD OF THE INVENTION

The invention relates to pharmaceuticals and medicine, and in particular, to manufacturing and use of ophthalmic preparations comprising mitochondria-addressed antioxidants

BACKGROUND OF THE INVENTION

Oxidative stress is believed to be one of the key reasons for the development of different eye pathologies.

Mitochondria-addressed antioxidants that can be reduced and oxidized by the enzymes of the electron transport chain of mitochondria are one of the most effective antioxidants (see Skualchev V. P. (2005), *IUBMB Life*. 57:305-10; Skulachev V. P. (2007) *Biochemistry (Mosc.)* 72:1385-96; Antonenko Yu. N. et al. (2008) *Biochemistry (Mosc.)*73: 1273-87).

However, said mitochondrial antioxidants have some peculiarities that complicate their use in practice. One of the main peculiarity is the observation that the antioxidant efficiency of a compound depends on its dose and final concentration in mitochondria) in non-obvious way. At certain concentrations these substances can act as one of the most powerful prooxidants that can make mitochondria to produce a significant amount of reactive oxygen species (Antonenko Yu N. et al. (2008) *Biochemistry (Mosc.)*73: 1273-87; Doughan A. K. and Dikalov S. I. (2007) *Antioxid Redox Signal*. 9:1825-36).

A principle possibility of treating eye diseases with the mitochondria-addressed antioxidant SkQ1 was shown in application WO2008048134, and in more detail in a paper by Neroev et al., (2008) *Biochemistry (Mosc.)*73:1317-28. These sources report data on the treatment of some eye diseases with the aid of aqueous solutions of SkQ1. However, no ophthalmic pharmaceutical composition comprising mitochondria-addressed is disclosed at the moment. The unusual physicochemical properties of mitochondria-addressed antioxidants make such composition non-obvious. For example, some substances routinely used as part of numerous preparations,—eye drops, accelerate degradation of SkQ1. The ability of SkQ1 to be irreversibly absorbed at the surface of tubes (vials) containing eye drops was also detected. This leads to drastic and uncontrolled change in the concentration of active ingredients in a pharmaceutical composition that, for said reasons, can fundamentally alter the effectiveness of the composition (up to obtaining the results which are completely the opposite of desirable).

SUMMARY

The present disclosure provides, in one aspect, a pharmaceutical composition for treatment or prophylaxis of eye pathologies, comprising: a mitochondria-addressed antioxidant; a pH buffer; a mitochondrially-addressed antioxidant concentration stabilizer; a prolongator; an isotonic component; and a preservative. In some embodiments, the mitochondria-addressed antioxidant comprises: a targeting moiety; a linker group; and an antioxidant, having the chemical structure (I):

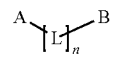

wherein:

A is an effector moiety—antioxidant optionally having a following structure:

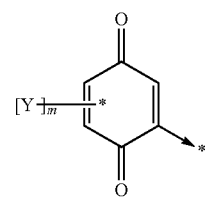

and/or reduced forms thereof, wherein:

m is an integer from 1 to 3; each Y is independently selected from the group consisting of: lower alkyl, lower alkoxy; or two adjacent Y groups, together with carbon atoms to which they are attached, form a following structure:

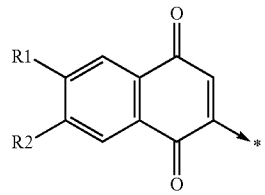

and/or reduced forms thereof, wherein:

R1 and R2 may be the same or different and are each independently lower alkyl or lower alkoxy; L is a linker group, comprising:

a) straight or branched hydrocarbon chain which can be optionally substituted by one or more substituents and optionally contains one or more double or triple bonds; and b) a natural isoprene chain;

n is integer from 1 to 40, preferably from 2 to 15, and particularly preferably from 5 to 11;

B is a targeting group comprising:

a) a Skulachev-ion Sk: $Sk^+Z^-$, wherein: Sk is a lipophilic cation; and Z is a pharmacologically-acceptable anion; and b) a charged hydrophobic peptide containing 2-20 amino acid residues, and solvates, salts, isomers or prodrugs thereof.

In one embodiment, n is an integer from 2 to 15, and in another embodiment, n is an integer from 5 to 11.

In some embodiments, the mitochondria-addressed antioxidant is SkQ1-bromide

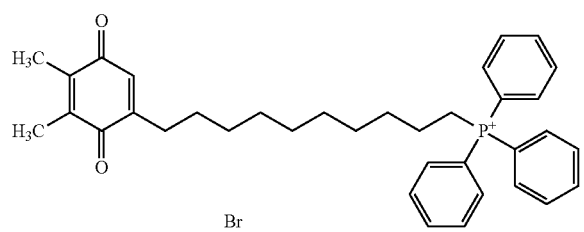 [SMILES: CC1=C(C)C(=O)C(CCCCCCCCCC[P+](c2ccccc2)(c2ccccc2)c2ccccc2)=CC1=O ; Br]

and/or reduced forms thereof.

In other embodiments, the mitochondria-addressed antioxidant is SkQ1-Cl, or SkQ1$_2$-SO$_4$.

In some embodiments, the pH buffer is a physiologically acceptable pH buffer comprising phosphate buffer, acetate buffer, borate buffer, carbonate buffer, citrate buffer, Tris buffer, glutamine buffer, epsilon-aminocaproic acid buffer, or combinations thereof.

In particular embodiments, the mitochondria-addressed antioxidant stabilizer prevents reversible and irreversible absorption of the mitochondrial addressed antioxidant on walls of a vial containing the pharmaceutical composition. In certain embodiments, the mitochondrial antioxidant concentration stabilizer comprises a benzalkonium salt, berberine, palmatine, tetraphenylphosphonium, tetrabutyl ammonium, or combinations thereof.

In some embodiments, the prolongator comprises a disaccharide, a trisaccharide, a polysaccharide, a water-soluble cellulose derivative. In particular embodiments, the water soluble cellulose derivative comprises methylcellulose, hydroxyethylcellulose, hydroxypropylmethylcellulose, carboxymethylcellulose, sodium chondroitin sulfate, sodium hyaluronate, or combinations thereof. In other embodiments, the prolongator comprises carboxyvinyl polymer, polyvinyl ethanol, polyvinylpyrrolidone, macrogol, or combinations thereof.

In certain embodiments, the isotonic component comprises sodium chloride, calcium chloride, glycerol, mannitol, sorbitol, boric acid, glucose, propylene glycol, or combinations thereof.

In some embodiments, the preservative comprises benzalkonium chloride, benzethonium chloride, chlorhexidine gluconate, chlorbutanol, benzyl ethanol, sodium dehydroacetate, parahydroxybenzoates, sodium edetate, boric acid etc.; sodium bisulfate, sodium thiosulfate, sodium edetate, sodium citrate, ascorbic acid, dibutyl hydroxy toluene, or combinations thereof.

In some embodiments, the pharmaceutical composition further comprising an active ingredient different than the mitochondria-addressed antioxidant, such as an antioxidant, an antiseptic, an astringent, a cautery, a resorbent, a hyposensitizer, an antibiotic, an anti-inflammatory preparation, an antibacterial, a sulfanilamide preparation, an antiviral preparation, a non-specific anti-inflammatory, a reparative preparation, a local anesthetic, a systemic ophthalmologic preparation, an anti-cataract preparation, a hypotensive antiglaucoma medical preparation, a cholinomimetic preparation, an anticholinesterase preparation, a sympathomimetic, an adrenergic preparation, an antiadrenergic preparation, a beta-adrenergic blocker, a prostaglandin, a carbonic anhydrase inhibitor, a mydriatic, a vitamin, and a vitamin analog, a natural cornea moisture restorer, or combinations thereof. In certain embodiments, the additional active ingredient simultaneously performs more than one function. For example, this additional active ingredient is also an antioxidant, a pH buffer, a mitochondrially-addressed antioxidant concentration, a stabilizer, a prolongator, an isotonic component, and/or a preservative.

In one embodiment, the pharmaceutical composition comprises: from 1 nM to 25000 nM of the mitochondrially-addressed antioxidant; from 0.1 mM to 1000 mM of the pH buffer, the pH buffer having a pH ranging from 4.5 to 8.5; from 0.0001% to 1% of the mitochondrially-addressed antioxidant concentration stabilizer; and from 0.001% to 1% (w/v) of the prolongator. In certain embodiments the pH buffer ranges from 1 mM to 100 mM, from 5 to 8, or from 6 to 7. In some embodiments, the stabilizer is present at from 0.01% to 0.2%.

In a particular embodiment, the pharmaceutical composition comprises, per 5 ml of solution: about 770 ng SkQ1-bromide; about 4.4 mg sodium dihydrophosphate; about 4.7 mg sodium hydrogen phosphate dodecahydrate; about 10 mg hydroxymethyl propyl methylcellulose; about 5 μg benzalkonium chloride; about 45 mg sodium chloride; and purified water to 5.0 ml.

In another aspect, the disclosure provides a method of treating an eye pathology, comprising administering to a subject afflicted with such an eye pathology a therapeutically-effective amount of the pharmaceutical composition. In some embodiments, the eye pathology is macular degeneration of the retina. In other embodiments, the eye pathology is cataract, senile cataract and/or diabetic cataract. In yet other embodiments, the eye pathology is a retinopathy, such as retinal detachment, detached retinal vessels, detached choroid, optic nerve retinopathy, optic nerve atrophy, central and peripheral chorioretinal dystrophies, or uveitis. In some embodiments, the eye pathology is intraocular hemorrhage or traumatic hemorrhage, or is an inflammatory disease, such as conjunctivitis, eye ulcer, keratitis, or dry keratoconjunctivitis. In yet another embodiment, the eye pathology is glaucoma.

DESCRIPTION OF THE INVENTION

This description provides a pharmaceutical composition (eye drops) which allows effective use of mitochondrial antioxidants for treatment of eye diseases in humans and animals.

In general, composition of eye drops is a solution comprising the following components (formula 1):

Component A1 is a mitochondria-addressed antioxidant;
Component A2 is a pH buffer;
Component A3 is a mitochondria-addressed antioxidant concentration stabilizer;
Component A4 is a prolongator (thickener);
Component A5 is an isotonic component; and
Component A6 is a preservative.

The therapeutic formulation also may optionally comprise one or more additional active ingredients (Component A7).

Component A1 is a compound comprising a targeting moiety, a linker group, and an antioxidant. The general chemical structure of these compounds can be described by a following structure (I):

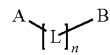

wherein:
A is effector moiety—antioxidant optionally having a following structure:

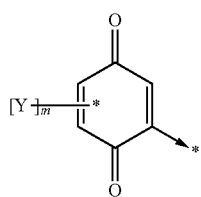

and/or reduced form thereof, wherein:
m is an integer from 1 to 3;
each Y is independently selected from the group consisting of: lower alkyl, lower alkoxy; or two adjacent Y groups, together with carbon atoms to which they are attached, form a following structure:

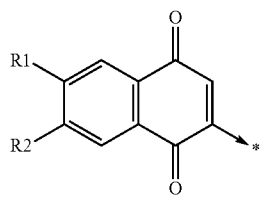

and/or a reduced form thereof, wherein:
R1 and R2 may be the same or different and are each independently Lower alkyl or lower alkoxy;
L is a linker group, comprising:
  a) a straight or branched hydrocarbon chain which can be optionally substituted by one or more substituents and optionally contains one or more double or triple bonds; and
  b) a natural isoprene chain;
n is integer from 1 to 40, from 2 to 15, or from 5 to 11;
B is a targeting group comprising:
  a) a Skulachev-ion Sk: $Sk^+Z^-$
  where Sk is a lipophilic cation and Z is a pharmacologically acceptable anion; and
  b) a charged hydrophobic peptide containing 2-20 amino acid residues, and/or solvates, salts, isomers or prodrugs thereof.

One of compounds for use as component A 1 is SkQ1-bromide:

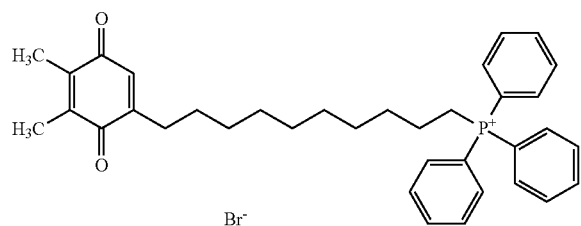 [SMILES: CC1=C(C)C(=O)C(CCCCCCCCCC[P+](c2ccccc2)(c2ccccc2)c2ccccc2)=CC1=O ; [Br-]]

and/or reduced forms thereof.

However, any other pharmacologically acceptable anion such as $Cl^-$, $SO_4^{2-}$ etc. may alternatively be selected as the anion.

Component A2 is a pH buffer comprising components pharmacologically acceptable in composition of eye drops. Buffers include phosphate buffer, acetate buffer, borate buffer, carbonate buffer, citrate buffer, Tris buffer, glutamine buffer, and epsilon-aminocaproic acid buffer.

Component A3 is a concentration stabilizer for the mitochondrial antioxidant Component A1, preventing reversible and irreversible sorption of component A1 on the walls of a vial containing the pharmaceutical composition. "Irreversible sorption" implies both irreversible interaction of component A1 with vial wall material and any chemical transformation of component A1 which occurs as a result of a local increase in its concentration near the vial walls. A compound which is a lipophilic cation ("Skulachev ion") of specific hydrophilic character (a benzalkonium ion with a pharmacologically acceptable anion (benzalkonium chloride), can be used as concentration stabilizer. It is also possible to use berberine, palmatine, tetraphenylphosphonium, tetrabutyl ammonium, and other similar compounds. Vial walls can optionally be chemically modified as follows. The concentration stabilizer can be covalently attached to the vial wall material. Also, in one embodiment, the vial wall material is selected in such a way that sorption (or interaction) of component A1 on the walls does not occur (or occurs but insignificantly). In this case, component A3 is not required.

Component A4 is a prolongator (thickener), added into the eye drops in order to: a) increase the viscosity of the solution and thus increase the time the medicine is present on the ocular surface; b) stabilize the concentration of active ingredient after instillation (prevention of volume reduction due to moisture loss); and c) increase stability of active ingredient during storage. Di-, tri- and poly-saccharides including water-soluble cellulose derivatives, such as methylcellulose, hydroxyethylcellulose, hydroxypropylmethylcellulose and carboxymethylcellulose, sodium chondroitin sulfate, sodium hyaluronate, carboxyvinyl polymer, polyvinyl ethanol, polyvinylpyrrolidone, and macrogol, etc. can be used as a prolongator.

Component A5 is an isotonic component that endows the composition with osmotic properties suitable for eye drops. Sodium chloride, calcium chloride, glycerol, mannitol, sorbitol, boric acid, glucose, propylene glycol etc. can be used as the isotonic component. Sodium chloride is the preferred isotonic component.

Components A6 is a preservative and optionally stabilizer of the eye drops, which can be selected from, but not limited to, the following compounds: benzalkonium chloride; enzethonium chloride; chlorhexidine gluconate; chlorbutanol; benzyl ethanol; sodium dehydroacetate; parahydroxybenzoates; sodium edentate; boric acid, etc.; sodium bisulfate; sodium thiosulfate; sodium edentate; sodium citrate; ascorbic acid; dibutyl hydroxy toluene, etc.

Some compounds can perform functions of several components simultaneously. For instance, in one embodiment 0.1% benzalkonium chloride simultaneously performs function of the mitochondrial antioxidant concentration stabilizer and the function of the antimicrobial preservative (i.e., it serves as both component A3 and component A6).

As part of a pharmaceutical composition, component A7 may constitute one and/or more compounds selected from the following groups of compounds which are both compounds, themselves, and names of preparations (and in this case is an active ingredient of corresponding preparation).

Useful active components include antioxidants, astringents and cauteries, resolving agents, and hyposensitizing antibiotics.

Useful antioxidants include N-acetyl cysteine, soluble vitamin E derivatives, ascorbic acid, mannitol, trolox, methylethylpiridinol, and taufon, etc.

Useful antiseptics include furacilinum, potassium permanganate (Kaliihypermanganicum), brilliant green (Viride Nitens), iodine solution ethanol, tincture of iodine (sol. jodi spirituosae, tinctura iodi 5%), Hydrogen peroxide (Sol. Hydrogeniiperoxididiluta), Novoimaninum, Collargolum, Resorcinol (Resorcinum), and Zinc sulfate (Zinci sulfas).

Useful astringents and cauteries include Tannin (Tanninum, Acidum tannicum), and Xeroform (Xeroformium).

Useful resolving agents include Ethylmorphine hydrochloride, dionin (Aethylmorphini hydrochloridum, dioninum), Oxygen (Oxygenium), Sodium iodide (Natrium jodidum), and Potassium iodide (Kalium jodidum), Lydasum).

Useful hyposensitizers include Alergoftal, Alomide, Spersallerg, Calcium chloride (Calcii chloridum), Calcium gluconate (Calcii gluconas), Diphenhydramine (Dimedrolum), Diprazinum, Pipolphen, Suprastin, Cusicrom, Maxidex, Prenacid, Lecrolyn, synonym Opticrom, and Hay-Crom).

Useful antibiotics include Benzylpenicillin sodium (potassium) salt (Benzyl-penicillinum-natrium, -kalium), Ampicillin trihydrate (Ampicillini trihydras), Ampicillin sodium salt (Ampicillinum-natrium), Methicillin sodium salt (Methicillinum-natrium), Tetracycline (Tetracyclinum), Metacycline hydrochloride, rondomycine (Methacyclinum hydrochloridum, Rondomycinum), Chloramphenicol (Laevomycetinum), Oletetrinum, Tetraolean, Sigmamycin, Synthomycin (Synthomycinum), Streptomycin sulfate (Streptomycini sulfas), Erythromycin (Erythromycinum), Gentamicin sulfate, garamycin (Gentamycini sulfas, Garamycin), Monomycin (Monomycinum), Neomycin (Neomycinum), Cefaloridinum, Ceporin, Lincomycin hydrochloride (Lincomycinum hydrochloridum), and Nystatin (Nystatinum).

Useful anti-inflammatory and antibacterial preparations for local use include Garasone, Dexagentamycin, Maxitrol, Tobradex, Vitabact, Picloxidine, Fucithalmic, Colbiocin, Eubetal, Okacin, Lomefloxacin, Cipromed, and Ciprofloxacin).

Useful sulfanilamide preparations include Sulfacyl-sodium, sulfacetamide (Sulfacylum-natrium), Sulfadimezin (Sulfadimezinum), Aethazol (Aethazolum), Sulfalen, sulfametopyrazine (Sulfalenum, Kelfizina), Sulfapyridazinum Sulfadimethoxin, and madribon (Sulfadimethoxinum).

Useful antiviral preparations include Idoxuridin, Kerecid, Oftan-IDU, Poludanum, Tebrophen (Tebrophenum), Florenal (Florenalum), Oxolin (Oxolinum), Deoxyribonuclease (Desoxyribonucleasa), Zovirax, Aciclovir, Valtrex, Valaciclovir, and Licopid).

Useful non-specific anti-inflammatory and reparative preparations include Amidopyrine, pyramidon (Amidopyrinum), Acetylsalicylic acid, aspirin (Acidumacetylsalicylicum), Phenylbutazone (Butadionum), Reopyrini, Indomethacin (Indometacinum), Pyrogenalum, Naclof, Diclo-F, and Diclofenac).

Useful local anesthetics include Cocaine hydrochloride (Cocaini hydrocloridum), Novocaine (Novocainum), Dicain (Dicainum), Trimecainum, and Inocainum).

Useful preparations for systemic use in ophthalmology include Glutamic acid (Acidumglutaminicum), Halidor, Dicynone, etamsylate Vinpocetini, vinpocetini-AKR1, cavinton, Trental, pentoxifylline, pentilin, pentomer, Solcoseryl, Taufon, taurine, Cerebrolysinum, and Emoxypine).

Useful anti-cataract preparations include Viceinum, Vitaiodurolum, vitaphacol, Qinax, Cysteine (Cysteinum), ATP, and adenosine triphosphate (Sol. Natrii adenosintriphosphatis).

Useful hypotensive anti-glaucoma medical preparations include Cholinomimetic preparations: Pilocarpine hydrochloride (Pilocarpini hydrochloridum), Carbachol (Carbacholum), Aceclidine (Aceclidinum), Anticholinesterase preparations: Armin (Arminum), Eserine (Eserinum), Proserin (Proserinum), Phosphacolum Tosmilen, demecarium bromide (Tosmilenum, Demecarii bromidum), Sympathomimetics—Adrenergic preparations: Adrenaline (Adrenalinum), eppy, epinephrine, Oftan-dipivefrin, Dipivalyl epiphrin, dipivephrin, Clophelin (Clophelinum), isoglaucon, Apraclonidin, iopidine, Antiadrenergic preparations—Beta-adrenergic blockers: Arutimol, timolol maleate, ocumed, optimol, timolol (Timololum), timolol-POS, blocarden, timoptic, Fotil, fotil-forte, Proxodolol, Betaxolol, betoptic, Prostaglandins: Latanoprost, xalatan, Combination therapies: Timpilo, Fotil, and Fotil-forte).

Useful carbonic anhydrase inhibitors include Diacarb, acetazolamide, Trusopt, dorzolamide hydrochloride (Dorzolamide hydrochloridum), and Rescula (unoprostone).

Useful mydriatics include, but are not limited to, Atropine sulfate (Atropini sulfas), Scopolamine hydrobromide (Scopolamini hydrobromidum), Homatropine hydrobromide (Homatropini hydrobromidum), Platyphylline hydrotartrate (Platiphyllini hydrotartras), Adrenaline hydrochloride (Adrenalinihydrochloridum) Phetanole (Phetanolum), Mydriacyl, tropicamid, Cyclomed Irifrin, and phenylephrine).

Useful vitamins and their analogs include Vitamin A, retinol (Vitaminum A, Retinolum), Fish oil (Oleum Jecoris Aselli), Citral (Citralum), Thiamine bromide (Thiamini bromidum), vitamin $B_1$, Vitamin $B_2$, riboflavin, riboflavin-mononucleotide, Riboflavinum, and Riboflavinum-mononucleotidum.

Useful natural cornea moisture restorers include Oftagel, carbomer, Corneregel, Tears naturale, Vitacic, Vidisic, and Lacrysin.

Concentrations of the components are as follows.

A1 is from 1 nM to 25000 nM.

A2 is of a concentration sufficient to stabilize the pH value in a desired range. The concentration is from 0.1 mM to 1000 mM, in the range from 1 mM to 100 mM. The desired pH range is determined based on the stability of component A1 and the pH optimum for eye drops, such as from 4.5 to 8.5, from 5 to 8, and from 6 to 7.

A3 is of a concentration determined experimentally and depends on the choice of a specific stabilizer. The molar concentration of the stabilizer may exceed the concentration of component A1. The excess may be from 10 to 1000000 times. The concentration of stabilizer is in the range from 0.0001% to 1%, and from 0.01% to 0.2%.

A4 is of a concentration determined on the basis of the accepted requirements for eye drops depending on the selected prolongator, preferably ranging from 0.001 to 1% (w/v).

A5 is of a concentration that ensures physiologically-acceptable osmotic properties of the solution (maximally close to the osmotic properties of eye fluid).

A6 is of a concentration of preservative depending on the choice of a particular preservative and can range from a minimum concentration that ensures the stability of the composition during storage, to a maximum concentration that has no harmful effect on eye tissues, such as on the cornea.

The concentration of an additional active ingredient (A7) is determined according to the pharmacological properties of a particular compound. The concentration may be reduced based on the enhancement of therapeutic effect by combining the additional active ingredient with the mitochondria-addressed antioxidant.

In an embodiment, a preferred pharmaceutical composition corresponding to Formula I is eye drops (per a vial containing 5 ml of eye drops) of the following composition (Table 1).

TABLE 1

Composition 1

| COMPONENT | AMOUNT PER 5 ML OF EYE-DROPS |
|---|---|
| SkQ1 - bromide | about 770 ng |
| Sodium dihydrophosphate | about 4.4 mg |
| Sodium hydrogen phosphate dodecahydrate | about 4.7 mg |
| Hydroxymethyl propyl methylcellulose | about 10 mg |
| Benzalkonium chloride | about 5 micrograms |
| Sodium chloride | about 45 mg |
| Purified water | to 5.0 ml |

In composition 1, SkQ1-bromide is the following compound with a pharmacologically-acceptable degree of purity.

SkQ1

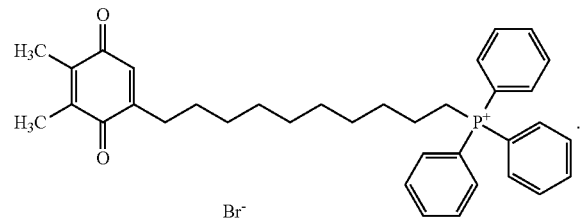

An aspect of this disclosure is the fact that the active ingredient of the composition is rather stable, and its absorption on the surface of vials is prevented (see the experimental Example 1). Also, as compared to a simple aqueous solution of SkQ1, the composition comprises a polymer prolongator chemically compatible with SkQ1. Not all of the polymers routinely used in the composition of eye drops appeared to be compatible with SkQ1, and some polymers destabilized the compound (see Example 1).

Eye drops prepared in accordance with the above formula are effective in treating a variety of eye diseases in humans and animals (see examples). Therefore, an aspect is the use of the eye drops for treatment of patients suffering from different eye pathologies, as well as for prophylaxis of these pathologies.

"Different eye pathologies" comprise cataract, glaucoma, eye inflammation diseases (including autoimmune), different forms of macular degeneration (MD), and other related symptoms such as atrophic (dry) MD, exudative (wet) MD, age-related maculopathy (ARM), choroidal neovascularization, detached pigment retinal epithelium (PED), and atrophy of the pigment retinal epithelium (RPE).

The term "macular degeneration (MD)" also comprises all eye diseases irrelevant to age-related changes in a human organism such as vitelliform degeneration of Best, Stargardt disease, juvenile macular dystrophy, Behr's disease, Sorsby's dystrophy, and Doyne honeycomb retinal dystrophy.

"Symptoms related to macular degeneration" comprise drusen surrounded by white-yellow spots, submacular discoid scar of tissues, choroidal neovascularization, detached pigment retinal epithelium (PED), atrophy of pigment retinal epithelium (RPE), anomalous expansion of choroidal blood vessels, blurred or disturbed vision area, central dead point, pigment anomalies, mixed layer of thin granulation located on the inner side of Bruch's membrane, and thickening and lowered permeability of Bruch's membrane.

The composition can be used for effective prophylaxis or treatment of all forms of macular degeneration and other related syndromes or symptoms, regardless of their causes. The causes of macular degeneration include genetic or physical trauma, diseases such as diabetes, or infections, in particular, bacterial. In one aspect of the invention the patient is human, and in another aspect of the invention, the patient is a domestic animal (dog, cat, horse or other). In this case, the composition is used as a veterinary preparation.

Reference will now be made to specific examples illustrating the disclosure. It is to be understood that the examples are provided to illustrate exemplary embodiments and that no limitation to the scope of the disclosure is intended thereby.

EXAMPLES

Example 1

Stability of Active Ingredient in Pharmaceutical Composition (Composition 1)

In this stability study of aqueous solutions of SkQ1 (10 mM sodium phosphate, pH 6.5, 0.9% NaCl) in concentration ranges up to 250 nM, the addition of 0.01% benzalkonium chloride prevents a decrease in the concentration of active ingredient during storage for 24 hours at room temperature (see Table 2).

TABLE 2

Stability of SkQ1 in Solutions Containing Benzalkonium Chloride

| Concentration of benzalkonium chloride, % | Added concentration of SkQ1, nM | Determined concentration of SkQ1 in 24 hours, nM | Relative content of SkQ1, % |
|---|---|---|---|
| 0 (control) | 250 | 104 | 42 |
| 0.01 | 250 | 254 | 102 |
| 0.01 | 180 | 180 | 100 |
| 0.01 | 100 | 97 | 97 |
| 0.01 | 50 | 56 | 112 |

These data show that in the absence of benzalkonium chloride, the concentration of SkQ1 decreases by 58%. This phenomenon is completely prevented by addition of 0.01% benzalkonium chloride, irrespective of the initial concentration of SkQ1.

A comparison of the effect of the two prolongators used in eye drops, methylcellulose (MC) and hydroxypropyl methylcellulose (HPMC), on the stability of aqueous solutions of SkQ1 (10 mM sodium phosphate, pH 6.5, 0.9% NaCl, 0.01% benzalkonium chloride) shows that only the addition of 0.2% HPMC stabilizes the concentration of the active ingredient during storage for 50 days at room temperature (see Table 3).

TABLE 3

Stability of SkQ1 in Solutions With Different Prolongators

| Content of prolongators | Relative content of SkQ1 after incubation for 50 days, % |
|---|---|
| 0.2% HPMC | 93 |
| 0.2% MC | 79 |

TABLE 3-continued

Stability of SkQ1 in
Solutions With Different Prolongators

| Content of prolongators | Relative content of SkQ1 after incubation for 50 days, % |
|---|---|
| control | 83 |

Materials and Method for Quantitative Detection of SkQ1

Analysis is carried out by high-performance liquid chromatography with MS/MS detection.

The following is placed in a flask with a capacity of 1000 ml: 0.78 ml (920 mg) of formic acid, 50 ml of acetonitrile, and the volume is adjusted to the mark with Milli-Q water and mixed thoroughly. The solution is effective for one week.

The following is placed in a flask with a capacity of 1000 ml: 0.78 ml (920 mg) of formic acid, and the volume is adjusted to the mark with acetonitrile and is mixed thoroughly. The solution is effective for one week.

A. 0.5 M Solution of 3-chloroperbenzoic Acid in Ethanol.

12.4 g of 3-chloroperbenzoic acid is placed in a flask with a capacity of 100 ml. 50 ml of 96% ethanol is added and the mixture stirred. The solution is brought to volume with 96% ethanol and stirred.

B. Internal Standard Solution.

12.65 mg of SkQ1 labeled with 15 atoms of deuterium (SkQ1-d15) is dissolved in 1 ml of ethanol 96% and transferred quantitatively into a flask with a capacity of 100 ml. The volume is adjusted to the mark with 96% ethanol and mixed thoroughly (solution 1). The solution is stored at −80° C. for up to 1 year. 0.5 ml of the resulting solution is transferred to a flask with a capacity of 100 ml, and the volume is adjusted to the mark with ethanol 96%. The solution is stored at a temperature of −24° C. for up to 3 days.

C. Original Standard Solution.

50 mg of SkQ1 bromide is dissolved in 1 ml of 96% ethanol and transferred quantitatively into a flask with a capacity of 50 ml. The volume of solution is adjusted to the mark with the same solvent (solution 1). This solution is stored at −80° C. for up to 3 months. 1 ml of the solution is transferred to a flask with a capacity of 10 ml, and the volume is adjusted to the mark with ethanol 96% (solution 2). 0.77 ml of solution 2 is transferred to a flask with a capacity of 50 ml, and the volume is adjusted to the mark with ethanol 96% (original standard solution). The solution 2 and original standard solution is stored at a temperature of −24° C. for up to 3 days.

D. A Solution of Standard Sample (SS).

1 ml of the original standard solution is placed into a flask with a capacity of 10 ml and the volume is adjusted to the mark with water-ethanol solution (solution A). 0.1 ml of the original standard solution is placed into a flask with a capacity of 10 ml. 5 ml of the water-ethanol solution is added and stirred for 11 min. 0.5 ml of solution A is added to 0.1 ml of an 0.5 M solution of 3-chloroperbenzoic acid in ethanol, and the volume is adjusted to the mark with ethanol-water solution and stirred for 30 min. 1 ml of the derived solution is transferred into a chromatographic vial. The solution must be freshly prepared before use.

E. Water-ethanol Solution.

Equal volumes of 96% ethanol and water are mixed.

F. Test Solution.

100 μL of the internal standard solution is placed into a 10 ml flask. 5 ml of the water-ethanol solution is added and stirred for 11 min. 500 μL of sample solution is added to 0.1 ml of a 0.5 M solution of 3-chloroperbenzoic acid in ethanol, and the volume is adjusted to the mark with ethanol-water solution and stirred for 30 min. 1 ml of the resulting solution is transferred into a chromatographic vial.

The chromatographic conditions are as follows: The device used is a Waters ACQUITY HPLC®. The column used is steel, 2.1×50 mm, filled with sorbent Acquity BEH C18, 1.7 μm (Waters, P/N 186002350) or equivalent. The column temperature is 35° C. The mobile phase is eluent A: 20 mM solution of formic acid in 5% aqueous acetonitrile and eluent B: 20 mM solution of formic acid in aqueous acetonitrile. The flow rate is 0.5 ml/min. The volume of injection is the total loop (about 11 μL). The elution mode is a gradient of eluents A and B according to Table 4.

TABLE 4

| Time (min.): | % eluent A: | % eluent B: |
|---|---|---|
| 0.0 | 60 | 40 |
| 4.0 | 20 | 80 |
| 4.1 | 60 | 40 |
| 5.0 | 60 | 40 |

The time of the analysis is about 5 min. The detector is a Waters TQD (tri-quadrupole) for MS/MS.

The conditions of detection is as follows: The electrospraying mode is positive (ES+). The working mode is monitoring of reactions of settled ions (MRM). The temperature of the ion source is 120° C. The vaporization temperature is 450° C. The cone voltage is 55 V. The capillary voltage is 3.0 kV. The collision gas (CID) is argon. The collision gas flow rate is 0.18 ml/min. The collision gas pressure (CID) is $4.5 \times 10^{-3}$ mbar. The transitions of scans and collision energy are according to Table 5.

TABLE 5

| No. | Transitions scan (daltons) | Collision energies, eV | Substance: |
|---|---|---|---|
| 1 | 537.30 > 262.13 | 50 | SkQ1 |
| 2 | 537.30 > 289.12 | 50 | SkQ1 |
| 3 | 552.40 > 274.20 | 50 | SkQ1-d15 |
| 4 | 552.40 > 304.30 | 50 | SkQ1-d15 |

Solution of SS and the test solution should be chromatographed.

G. Suitability of the Chromatographic System.

The chromatographic system is suitable if: 1) the MRM chromatogram of SkQ1-d15 asymmetry factor of the main peak is not more than 2; 2) the effectiveness of the chromatographic column on the main peak is not less than 3000 theoretical plates; and 4) the relative standard deviation of the ratio of SkQ1 and SkQ1-d15 peak areas on the chromatograms of the solution is no more than 15%.

The SkQ1 content in the product (μg/ml) was calculated using the equation:

$$X = \frac{a \cdot (100 - W) \cdot P \cdot S/S_{smpl}}{1000000 \cdot S/S_{std}} \text{ wherein}$$

"$S/S_{smpl}$" is the ratio of peak areas and SkQ1 and SkQ1-d15 in chromatograms of the sample solution;

"S/S$_{std}$" is the ratio of SkQ1 and SkQ1-d15 peak areas in chromatograms of the SS solution;

"a" is the amount of SkQ1 taken to prepare the original standard solution, in mgs;

"W" is the water content and organic solvents in SkQ1 substance taken to prepare the original standard solution, in percent; and "P" is the SkQ1 content in SkQ1 substance taken to prepare the original standard solution, in percent.

Example 2

Use of Pharmaceutical Composition in Veterinary Practice

The species and breed of animal is a dog, Zverg Schnauzer (miniature schnauzer), male, born in 2005 (4 years old). It was admitted on Dec. 4, 2008.

The case history is as follows. The dog has been blind since November 2008. Since 2007, the dog could not see in the darkness. Now the dog can only keep itself oriented by sound. The owner believes that the animal has been ill for 1 year. The owner drew attention to changes in the animal's behavior during an evening stroll. The dog does not recognize the owner in a group of 5-6 people. The dog keeps itself poorly oriented during the daytime and stumbles upon objects. The dog recognizes the owner only by voice. In the dark the dog keeps itself oriented by sound.

This was the primary visit. Investigations have not been conducted earlier. The exact diagnosis was not given in a previous diagnosis. There was no previous treatment. This clinical case is hereditary.

The general condition of the animal at admission is satisfactory. The dog does not see. External examination shows that the eyelids have normal volume. The palpebral fissure is normal, the conjunctiva is pale pink, the cornea is shiny, spherical, transparent, moist, and contains no blood vessels. The anterior chamber is deep. The reaction of iris to light is absent.

The preliminary diagnosis is generalized progressive retinal atrophy, with no complications of the disease, and no concomitant diseases.

The examination results were as follows: Specific tests used were labyrinth, reaction to a cotton ball, and reaction to light. In the test with a labyrinth, the dog stumbled into obstacles both in darkness and in the light; it did not react to a cotton ball falling nearby; and the reaction of the iris to light was absent. The instrumental tests used were tests for leptospirosis, retinography and retino-photography. The test for leptospirosis produced negative results. For retinography, results see Table 4. Retino-photography revealed color change and hyper-reflection of the *tapetum lucidum*, and thinning of optic disc vessels. The optic disc color was white.

The clinical diagnosis is generalized progressive retinal atrophy, stage 2. Major symptoms are: blindness; the surface of *t. lucidum* is altered and hyper-reflective; small vessels of the retina are absent; and thinning of large vessels of the retina. The type of the disease is chronic. There is vision dysfunction in darkness and on light. The animal does not see large stationary or moving objects.

The prescribed treatment is the pharmaceutical composition (Composition 1) in a dose of 1 drop twice a day. The record of the treatment is shown in Table 6.

TABLE 6

Clinical Records of Clinical Case 1

| Date | Methods of investigation (tests) | Test resutls | Prescribed therapy |
|---|---|---|---|
| Dec. 4, 2008 | 1. Labyrinth | Negative | Pharmaceutical composition |
|  | 2. Reaction to a cotton ball | Negative |  |
|  | 3. Reaction to light | Negative (mydriasis). | (composition 1) |
|  | 4. Retinography | See Appendix | in a dose of 1 |
|  | 5. Retino-photography | Carpet area of t. Lucidum is hyper-reflex, small vessels of retina are absent, thinning of great vessels, OD is white. | drop once a day. |
|  | Retinogram | Right eye: A-wave - 56.5 micro Volts. B-wave - 9.5 micro Volts. Left eye: A-wave - 9.4 micro Volts, B-wave - 15 micro Volts |  |
| Dec. 24, 2008 | 1. Labyrinth | Negative |  |
|  | 2. Reaction to a cotton ball | +Negative |  |
|  | 3. Reaction to light | Positive Fundus of eye is unchanged. The dog no longer stumbled upon objects during the daytime, at night the dog does not see. According to the words of the mistress, the dog began to keep itself oriented better, especially during the daytime. | 1 drop once a day. |
| Apr. 13, 2009 | 1. Labyrinth | Positive |  |
|  | 2. Reaction to a cotton ball | Positive |  |
|  | 3. Reaction to light | Positive Vision is preserved, the dog sees, keeps itself well-oriented in any time of day. Tests are positive. Vision is preserved. |  |

TABLE 6-continued

Clinical Records of Clinical Case 1

| Date | Methods of investigation (tests) | Test resutls | Prescribed therapy |
|---|---|---|---|
| | Retinography | Right eye: A-wave - 56.5 micro Volts. B-wave - 203.5 micro Volts. Left eye: A-wave - 45 micro Volts, B-wave - 45.5 micro Volts | |

A dog, Zverg Schnauzer (miniature schnauzer) breed, nickname Vintik, age of 4 years, was admitted to the clinic Apr. 12, 2008. As a result of the acquisition of anamnesis data, clinical examination revealed a generalized progressive retinal atrophy. The dog cannot see. Blindness is observed for 1 year, carpet area of t. lucidum is hyper-reflective, small vessels of retina are absent, thinning of great vessels, OD is white.

The prescribed treatment is Composition 1 eye-drops, 1 drop twice a day. After 20 days of treatment the dog began to see better during the daytime. After 2 months of treatment the dog began to see during the daytime and in the darkness. Tests became positive.

The clinical picture of the eye fundus is unchanged. For retinography results see Table 7.

TABLE 7

Retinography Results

| Date | Right Eye | Left Eye |
|---|---|---|
| Dec. 4, 2008 | A-wave - 56.5 micro Volts. B-wave - 9.5 micro Volts. | A-wave - 9.4 micro Volts, B-wave - 15 micro Volts |
| Apr. 13, 2009 | A-wave - 56.5 micro Volts. B-wave - 203.5 micro Volts. | A-wave - 45 micro Volts, B-wave - 45.5 micro Volts |

Example 3

Use of Pharmaceutical Composition in Combination Therapy of Eye Diseases of Domestic Animals The following testing was done on dogs treated with Composition 1.

Test 1

A dog, 9 years old, nonpedigreed, was admitted to the clinic in late January 2009 with signs of hemorrhagic chorioretinitis and papillitis. At the time of examination the animal cannot see, and persistent mydriasis has been detected.

Since January 2009, the following treatment was applied: Dexamethasone (methylated fluoroprednisolone) 0.1% eye drops, 1 drop 4 times a day; after 10 minutes, pharmaceutical composition (Composition 1), eye drops, 1 drop once a day; after 10 minutes Emoxypine (Methylethylpiridinol) 1%, eye drops, 1 drop 3 times a day.

On Mar. 16, 2009, that the animal began to see was confirmed by the appearance of an electroretinogram signal. After that, only the pharmaceutical composition (Composition 1) (without additional preparations) was used as the maintenance therapy.

Test 2

A dog, 11 years old, Labrador (retriever) was admitted to the clinic in September 2008 with a diagnosis of uveodermatological syndrome (endogenous uveitis induced by autoimmune dermatitis). At the time of examination the animal cannot see.

The following treatment was applied: Cyclomed, eye drops, 1 drop twice a day; after 10 minutes Prenacid, eye drops, 1 drop once a day; after 10 minutes Indocollyre, eye drops, 1 drop twice a day, after 10 minutes Betoptic, eye drops, 1 drop 3 times a day; after 10 minutes Pharmaceutical composition (composition 1), eye drops, 1 drop once a day; after 10 minutes Emoxypine 1% eye drops, 1 drop 3 times a day.

On 30 Jan. 2009, electroretinography showed that the functional activity of the retina was very good. The animal can see. In the treatment of uveitis, significant remission of the disease was observed, but full recovery cannot be achieved due to the chronic type of the disease. Maintenance therapy with the aid of the pharmaceutical composition (Composition 1) was continued.

Test 3

A dog, 7 years old, German Shepherd, was admitted to the clinic in September 2008 with a diagnosis of endogenous uveitis induced by leptospirosis. Eyesight was preserved.

The following treatment was administered: Prenacid, eye drops, 1 drop once a day; after 10 minutes Indocollyre, eye drops, 1 drop twice a day; after 10 minutes Betoptic, eye drops, 1 drop 3 times a day; after 10 minutes Pharmaceutical composition (composition 1), eye drops, 1 drop once a day; after 10 minutes Emoxypine 1%, eye drops, 1 drop 3 times a day.

The treatment was completed in November 2008 and resulted in full recovery.

EQUIVALENTS

Those skilled in the art will recognize, or be able to ascertain, using no more than routine experimentation, numerous equivalents to the specific composition and procedures described herein. Such equivalents are considered to be within the scope of this invention, and are covered by the following claims.

The invention claimed is:

1. A pharmaceutical formulation for treatment or prophylaxis of eye pathology, comprising:
   (a) from 1 nm to 25000 nm of a mitochondria-addressed antioxidant comprising:

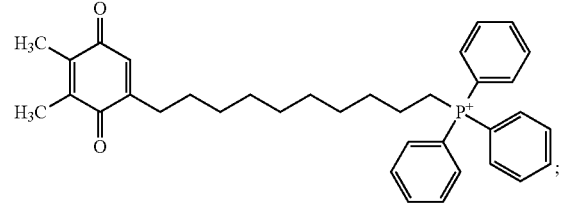

SkQ1

-continued

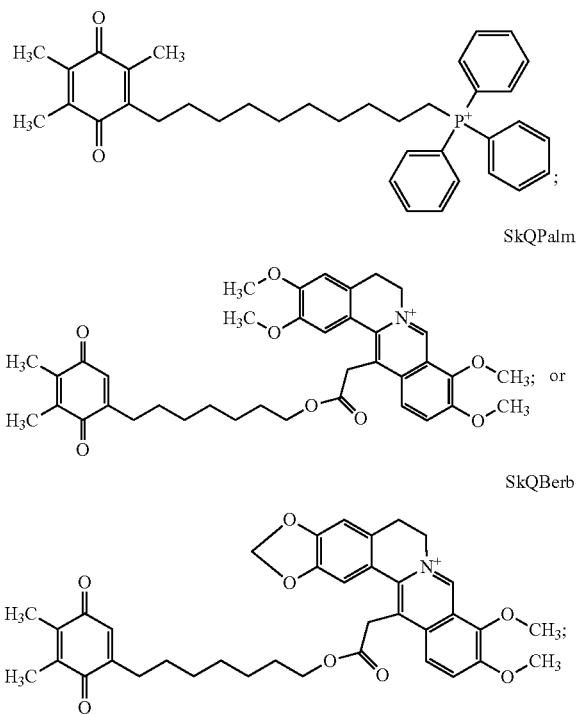

(b) from 0.01% to 0.2% of a lipophilic, cationic concentration stabilizer that stabilizes a concentration of the mitochondria-addressed antioxidant by preventing reversible and irreversible absorption of the antioxidant to walls of a vial containing the pharmaceutical composition, the stabilizer comprising a benzalkonium salt, berberine, palmatine, tetraphenylphosphonium, tetrabutyl ammonium, or combinations thereof; and (c) from 0.001% to 1% of a prolongator comprising a disaccharide, a trisaccharide, a polysaccharide, methylcellulose, hydroxyethylcellulose, hydroxypropylmethylcellulose, carboxymethylcellulose, sodium chondroitin sulfate, sodium hyaluronate, carboxyvinyl polymer, polyvinyl ethanol, polyvinylpyrrolidone, macrogol, or combinations thereof.

2. The pharmaceutical formulation of claim 1, wherein the mitochondria-addressed antioxidant is SkQ1-Br, SkQ1-Cl, or $SkQ1_2$-$SO_4$.

3. The pharmaceutical formulation of claim 1, further comprising a physiologically acceptable pH buffer comprising a phosphate buffer, an acetate buffer, a borate buffer, a carbonate buffer, a citrate buffer, a Tris buffer, a glutamine buffer, an epsilon-aminocaproic acid buffer, or combinations thereof.

4. The pharmaceutical formulation of claim claim 1, wherein the water soluble cellulose derivative comprises methylcellulose, hydroxyethylcellulose, hydroxypropylmethylcellulose, carboxymethylcellulose, sodium chondroitin sulfate, sodium hyaluronate, or combinations thereof.

5. The pharmaceutical formulation of claim 1, further comprising an isotonic component comprising sodium chloride, calcium chloride, glycerol, mannitol, sorbitol, boric acid, glucose, propylene glycol, or combinations thereof.

6. The pharmaceutical formulation of claim 1, further comprising an active ingredient different than the mitochondria-addressed antioxidant, the additional active ingredient being an antioxidant, an antiseptic, an astringent, a cautery, a resorbent, a hyposensitizer, an anti-biotic, an anti-inflammatory preparation, an antibacterial, a sulfanilamide preparation, an antiviral preparation, a non-specific anti-inflammatory, a reparative preparation, a local anesthetic, a systemic ophthalmologic preparation, an anti-cataract preparation, a hypotensive anti-glaucoma medical preparation, a cholinomimetic preparation, an anticholinesterase preparation, a sympathomimetic, an adrenergic preparation, an antiadrenergic preparation, a beta-adrenergic blocker, a prostaglandin, a carbonic anhydrase inhibitor, a mydriatic, a vitamin, and a vitamin analog, a natural cornea moisture restorer, or combinations thereof.

7. The pharmaceutical formulation of claim 1 comprising, per 5 ml of solution:
about 770 ng SkQ1 bromide;
about 4.4 mg sodium dihydrophosphate;
about 4.7 mg sodium hydrogen phosphate dodecahydrate;
about 10 mg hydroxypropylmethylcellulose;
about 5 µg benzalkonium chloride;
about 45 mg sodium chloride; and
purified water to 5.0 ml.

8. The pharmaceutical formulation of claim 1, wherein the lipophilic, cationic concentration stabilizer comprises benzalkonium chloride, benzethonium chloride, berberine, palmatine, tertraphenylphosphonium, tertrabutyl, ammonium, or combinations thereof.

* * * * *